(12) United States Patent
Runkana et al.

(10) Patent No.: US 12,102,941 B2
(45) Date of Patent: Oct. 1, 2024

(54) METHODS AND SYSTEMS FOR DETERMINING MULTI-COLUMN CHROMATOGRAPHY PROCESS CONFIGURATION

(71) Applicant: Tata Consultancy Services Limited, Mumbai (IN)

(72) Inventors: Venkataramana Runkana, Pune (IN); Venkata Sudheendra Buddhiraju, Pune (IN); Aditya Pareek, Pune (IN); Vishnu Swaroopji Masampally, Pune (IN); Karundev Premraj, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 642 days.

(21) Appl. No.: 17/383,117

(22) Filed: Jul. 22, 2021

(65) Prior Publication Data
US 2022/0040598 A1    Feb. 10, 2022

(30) Foreign Application Priority Data
Jul. 24, 2020    (IN) .............................. 202021031780

(51) Int. Cl.
*B01D 15/38*    (2006.01)
*B01D 15/18*    (2006.01)
(Continued)

(52) U.S. Cl.
CPC ..... *B01D 15/3809* (2013.01); *B01D 15/1885* (2013.01); *C07K 1/16* (2013.01); *C07K 1/36* (2013.01); *G01N 30/466* (2013.01)

(58) Field of Classification Search
CPC ........ C07K 1/16; C07K 1/36; G01N 30/8662; G01N 30/466; B01D 15/1885; B01D 15/3809
See application file for complete search history.

(56) References Cited

U.S. PATENT DOCUMENTS

| | | | | |
|---|---|---|---|---|
| 10,843,104 B2 * | 11/2020 | Lacki | ................... | G01N 30/465 |
| 10,948,483 B2 * | 3/2021 | Muller-Spath | ..... | B01D 15/3804 |
| 11,841,349 B2 * | 12/2023 | Tipler | .................. | G01N 30/466 |

OTHER PUBLICATIONS

Schmolder, Johannes et al., "A Modular Framework for the Modelling and Optimization of Advanced Chromatographic Processes", Processes, Jan. 2020, MDPI, https://www.researchgate.net/publication/338377245 A Modular Framework for the Modelling and Optimization of Advanced Chromatographic Processes/link/5e0fe22ca6fdcc2837562b3e/download.

(Continued)

*Primary Examiner* — An H Do
(74) *Attorney, Agent, or Firm* — FINNEGAN, HENDERSON, FARABOW, GARRETT & DUNNER LLP

(57) ABSTRACT

The disclosure generally relates to methods and systems for determining multi-column chromatography process configuration for capturing antibodies. Conventional approaches for design of MCC configuration are limited to rule based, either driven by UV spectroscopic measurements or by performing number of experiments, which involves a lot of material costs and time utilization. The present disclosure solves the technical problem of identifying the operational conditions that optimized the MCC process and the MCC configuration. A multi-objective optimization function defined with one or more decision variables associated with the operating conditions is considered to determine the optimal MCC configuration, while satisfying purification goals. The one or more key performance measures of the MCC process comprises a productivity, a capacity utilization, a product yield, and a product purity. The significant amount of time and the material cost invested for designing the optimum MCC configuration is decreased by the present disclosure.

15 Claims, 6 Drawing Sheets

(51) Int. Cl.
*C07K 1/16* (2006.01)
*C07K 1/36* (2006.01)
*G01N 30/46* (2006.01)

(56) References Cited

OTHER PUBLICATIONS

Zobel-Roos, Steffen et al., "Evaluating the performance of different multicolumn setups for chromatographic separation of proteins on hydrophobic interaction chromatography media by a numerical study", ANTIBODIES, Mar. 2018, vol. 7 (1), MDPI, https://www.mdpi.com/2073-4468/7/1/13/htm.

Zobel-Roos, Steffen et al., "Evaluation of Continuous Membrane Chromatography Concepts with an Enhanced Process Simulation Approach", Antibodies, Mar. 2018, vol. 7 (1), NCBI, https://www.researchgate.net/publication/323847278 Evaluation of Continuous Membrane Chromatography Concepts with an Enhanced Process Simulation Approach/link/5aaf7412aca2721710tc916d/download.

Gjoka, Xhorxhi et al., "A straightforward methodology for designing continuous monoclonal antibody capture multi-column chromatography processes", Journal of Chromatography A, Oct. 2015, vol. 1416, pp. 38-46, Elsevier, https://daneshyari.com/article/preview/1199085.pdf.

NG[a], Candy K.S. et al., "Design of high productivity sequential multi-column chromatography for antibody capture", Food and Bioproducts Processing, Apr. 2014, vol. 92, Issue 2, pp. 233-241, Elsevier, https://daneshyari.com/article/preview/18994.pdf.

\* cited by examiner

METHODS AND SYSTEMS FOR DETERMINING MULTI-COLUMN CHROMATOGRAPHY PROCESS CONFIGURATION

PRIORITY CLAIM

This U.S. patent application claims priority under 35 U.S.C. § 119 to: Indian Patent Application No. 202021031780, filed on 24 Jul. 2020. The entire contents of the aforementioned application are incorporated herein by reference.

TECHNICAL FIELD

The disclosure herein generally relates to the field of biopharmaceutical manufacturing, and, more particularly, to methods and systems for determining multi-column chromatography process configuration for capturing desired product such as antibodies.

BACKGROUND

Capture chromatography is a downstream processing approach that is used for separating for example, monoclonal antibodies from impurities such as host cell protein, host cell DNA that are present in a feed such as clarified cell culture fluid. The capture chromatography at commercial scale is usually performed in a batch mode (referred to as 'batch chromatography'), utilizing a single packed column to perform each operation of a set of chromatography operations including a load operation, a wash operation, a elute operation and an equilibration operation in series. This makes the batch chromatography highly inefficient in terms of productivity of the monoclonal antibodies and utilization of solid adsorbent resin due to a large processing time to perform starting from the loading operation to the equilibration operation through the same single packed column.

A multi-column chromatography (MCC) unit enables performance of the set of chromatography operations in parallel as it utilizes one or more columns through which the set of chromatography operations are distributed. This in turn helps reduce the processing time and thereby increases the productivity of the monoclonal antibodies and the utilization of the solid adsorbent resin. This also improves a recovery by reducing loss of the antibodies in the column breakthrough when some of the columns are interconnected while loading a feed. Conventional approaches for design of MCC configuration including a MCC unit, the set of chromatography operations, and determining its operating parameters are limited to rule based approaches, either driven by UV spectroscopic measurements or by performing a set of experiments to decide number of columns to be connected while receiving the feed. These involves a lot of material costs and time utilization. Also, conventional optimization techniques that optimize the design of the MCC configuration are limited and always comprise an area of improvement.

SUMMARY

Embodiments of the present disclosure present technological improvements as solutions to one or more of the above-mentioned technical problems recognized by the inventors in conventional systems.

In an aspect, there is provided a processor-implemented method comprising the steps of: receiving one or more of: feed characteristics, targets for some of one or more key performance measures of the MCC process, one or more MCC configurations of the MCC process, one or more column characteristics of each column of one or more columns present in each MCC configuration, and media characteristics of one or more chromatography media for use in each column of one or more columns; selecting a chromatography column (CC) process model set from a plurality of CC process model sets, based on the media characteristics of the one or more chromatography media for use in each column of the one or more columns and one or more components present in the feed, wherein each CC process model set comprises (i) a mobile phase mass transfer model and associated mobile phase model parameter (ii) a stationary phase mass transfer model and associated stationary phase parameters, and (iii) an adsorption-desorption model and associated adsorption-desorption parameters; determining through an optimization technique, values of one or more decision variables that optimizes the one or more key performance measures of the MCC process, to obtain optimized values of the one or more key performance measures, for each MCC configuration of the one or more MCC configurations, using the selected CC process model set, wherein the one or more decision variables are associated with operating conditions to be maintained at each chromatographic operation of a set of chromatographic operations to be performed at each stage, and the one or more column characteristics of each column of one or more columns present in the MCC configuration; and determining the optimum MCC configuration out of one or more MCC configurations, based on the associated optimized values of the one or more key performance measures of the MCC process.

In another aspect, there is provided a system comprising: a memory storing instructions; one or more Input/Output (I/O) interfaces; and one or more hardware processors coupled to the memory via the one or more I/O interfaces, wherein the one or more hardware processors are configured by the instructions to: receive or more of: feed characteristics, targets for some of one or more key performance measures of the MCC process, one or more MCC configurations of the MCC process, one or more column characteristics of each column of one or more columns present in each MCC configuration, and media characteristics of one or more chromatography media for use in each column of one or more columns; select a chromatography column (CC) process model set from a plurality of CC process model sets, based on the media characteristics of the one or more chromatography media for use in each column of the one or more columns and one or more components present in the feed, wherein each CC process model set comprises (i) a mobile phase mass transfer model and associated mobile phase model parameter (ii) a stationary phase mass transfer model and associated stationary phase parameters, and (iii) an adsorption-desorption model and associated adsorption-desorption parameters; determine through an optimization technique, values of one or more decision variables that optimizes the one or more key performance measures of the MCC process, to obtain optimized values of the one or more key performance measures, for each MCC configuration of the one or more MCC configurations, using the selected CC process model set, wherein the one or more decision variables are associated with operating conditions to be maintained at each chromatographic operation of a set of chromatographic operations to be performed at each stage, and the one or more column characteristics of each column of one or more columns present in the MCC configuration; and determine the optimum MCC configuration out of one or more MCC configurations, based on the associated optimized values of the one or more key performance measures of the MCC process.

In yet another aspect, there is provided a computer program product comprising a non-transitory computer readable medium having a computer readable program embodied therein, wherein the computer readable program, when executed on a computing device, causes the computing device to: receive or more of: feed characteristics, targets for some of one or more key performance measures of the MCC process, one or more MCC configurations of the MCC process, one or more column characteristics of each column of one or more columns present in each MCC configuration, and media characteristics of one or more chromatography media for use in each column of one or more columns; select a chromatography column (CC) process model set from a plurality of CC process model sets, based on the media characteristics of the one or more chromatography media for use in each column of the one or more columns and one or more components present in the feed, wherein each CC process model set comprises (i) a mobile phase mass transfer model and associated mobile phase model parameter (ii) a stationary phase mass transfer model and associated stationary phase parameters, and (iii) an adsorption-desorption model and associated adsorption-desorption parameters; determine through an optimization technique, values of one or more decision variables that optimizes the one or more key performance measures of the MCC process, to obtain optimized values of the one or more key performance measures, for each MCC configuration of the one or more MCC configurations, using the selected CC process model set, wherein the one or more decision variables are associated with operating conditions to be maintained at each chromatographic operation of a set of chromatographic operations to be performed at each stage, and the one or more column characteristics of each column of one or more columns present in the MCC configuration; and determine the optimum MCC configuration out of one or more MCC configurations, based on the associated optimized values of the one or more key performance measures of the MCC process.

In an embodiment, the optimal MCC configuration along with the values of one or more decision variables associated with the optimized values of the one or more key performance measures are displayed.

In an embodiment, selecting the CC process model set from the plurality of CC process model sets, comprises: determining CC model parameters of each CC process model set, based on a set of source data comprising residence time distribution data, adsorption kinetics data, adsorption equilibrium data and column breakthrough data, wherein the CC model parameters of the associated CC process model set comprises the associated mobile phase model parameter, associated stationary phase parameters and associated adsorption-desorption parameters; determining an error metric of each CC process model set, by comparing model predictions obtained from the determined CC model parameters with experimental data; and selecting the CC process model set having a least error metric.

In an embodiment, determining the values of the one or more decision variables that optimizes the one or more key performance measures of the MCC process to obtain the optimized values of the one or more key performance measures, for each MCC configuration of the one or more MCC configurations, comprises: (a) generating initial values of the one or more decision variables, using the optimization technique; (b) obtaining sequence of chromatographic operations and a duration of each sequence of chromatographic operations at each stage of the MCC process, if the initial values of the one or more decision variables satisfies a feasibility criteria, wherein the feasibility criteria is associated with completion of regeneration protocol during a column switch and completion of predefined number of wash volumes; (c) calculating the one or more key performance measures of the MCC process by simulating the MCC process using the selected CC model set for the obtained sequence of chromatographic operations and the duration of the sequence of chromatographic operations, at each stage, until a cyclic steady state (CSS) of the MCC configuration is achieved; (d) calculating a value of a multi-objective function defined as a weighted sum of some of the one or more key performance measures; (e) generating successive values of the one or more decision variables, using the optimization technique, based on the calculated value of the multi-objective function; (f) repeating steps (a) through (e), at each iteration, by considering the successive values of the one or more decision variables as the initial values, until either (i) a difference between the values of the multi-objective function for two successive iterations is less than a predefined threshold value or (ii) a predefined number of the iterations are performed, to determine the values of the one or more decision variables that optimizes the one or more key performance measures of the MCC process; and (g) obtaining the optimized values of the one or more key performance measures of the MCC process, based on the values of the one or more decision variables.

In an embodiment, the feed characteristics comprises of a feed composition comprising the one or more components, a feed flow rate and physical properties comprising a pressure, a temperature, a density and a pH value, the one or more key performance measures of the MCC process comprises a productivity, a capacity utilization, a product yield, and a product purity, the one or more column characteristics of each column comprises of a column length, a cross-sectional area of the column and a column porosity, and the characteristics of each chromatography media comprises of a particle size of resin, a particle porosity, a particle density and a static binding capacity.

In an embodiment, the associated mobile phase model parameter comprises a column dispersion coefficient, the associated stationary phase parameters comprises an effective diffusion coefficient in pores and an interfacial mass transfer coefficient, and the associated adsorption-desorption parameters comprises an adsorption rate constant and a desorption rate constant.

In an embodiment, the one or more decision variables associated with the operating conditions comprises a duration of each stage of MCC process, a pH value, a salt concentration, and a superficial velocity of process stream.

It is to be understood that both the foregoing general description and the following detailed description are exemplary and explanatory only and are not restrictive of the embodiments of the present disclosure, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
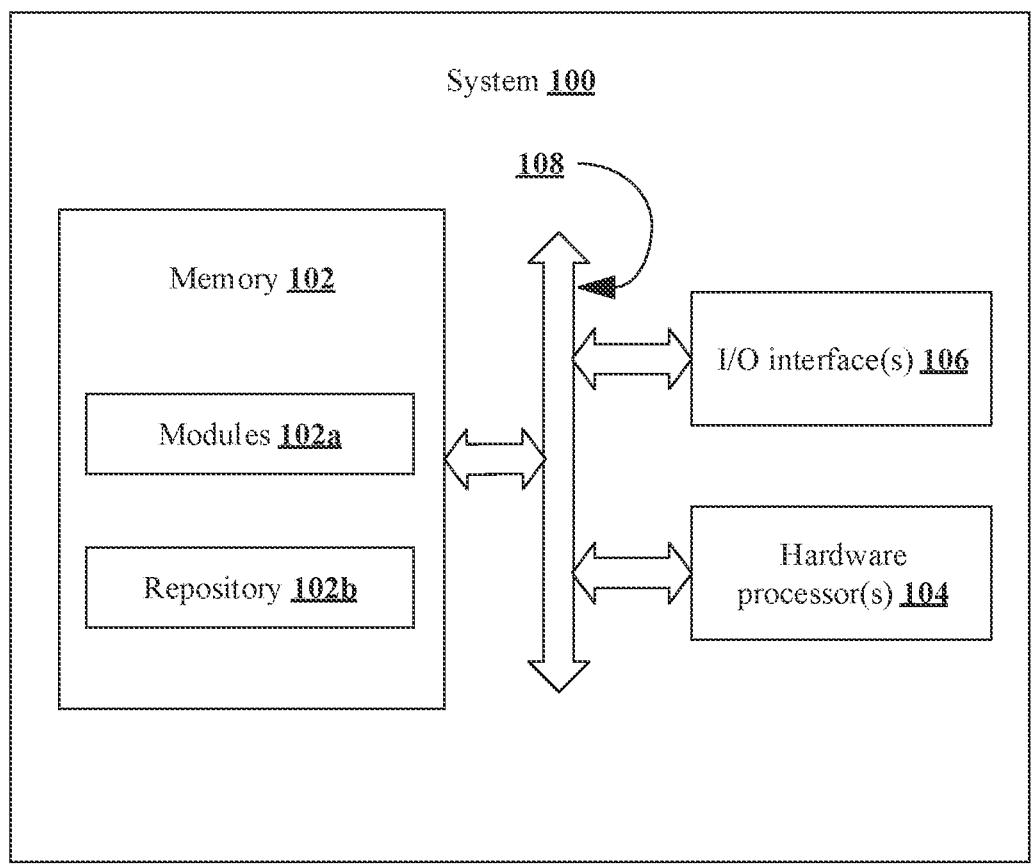
FIG. 1 is an exemplary block diagram of a system for determining an optimum multi-column chromatography (MCC) configuration of an MCC process, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Biopharmaceutical manufacturing in general is divided into upstream processing and downstream processing approaches for obtaining desired product, for example, monoclonal antibodies, from impurities. The upstream processing approach utilizes a bioreactor and a cell clarification equipment. The downstream processing approach utilizes a train of packed bed chromatography columns equipped with complementary stationary phases facilitate removal of product and process related impurities. Multiple technologies including a batch chromatography and a multi-column chromatography (MCC), are present in the downstream processing approach for separating monoclonal antibodies from impurities such as host cell protein, host cell DNA that are present in a feed such as clarified cell culture fluid. A set of chromatography operations including a load operation, a wash operation, a elute operation and an equilibration operation, may be performed at each stage of multiple stages utilizing one of the technologies for separating monoclonal antibodies.

In the batch chromatography, the set of chromatography operations are performed sequentially one after the other, in a single column (one column) and hence, the turnaround time is considerably long resulting in low productivity. Mass transfer resistances in the single column, both interfacial and intra-particle, may prevent dynamic binding capacity (defined in terms of amount of the product bound to the stationary phase under typical operating conditions) to be lower than static binding capacity. This further mandates loading the feed at reduced flow rates to circumvent loss of desired product yield. Moreover, the feed stream such as the clarified cell culture fluid from the reactor may not be loaded continuously onto the batch chromatography column, resulting in an additional requirement for a surge vessel.

Integrated continuous bioprocessing has been identified to be the next phase of evolution in the biopharmaceutical manufacturing domain. Multi-column counter current chromatography is one approach in this direction that aims to provide increased productivity and capacity utilization for capture of antibodies present in a feed. The multi-column chromatography (MCC) unit allows to perform the set of chromatography operations in parallel through multiple columns. The design of the multiple columns and the interconnections between the multiple columns is defined as an MCC configuration. Multi-column chromatography introduces additional decision variables such as a duration of each stage of the multiple stages.

Conventional multi-column chromatography designs are equipped with feedback controller that is driven by online UV spectroscopy measurements to determine the duration of each stage. Loading of the feed is stopped when the product concentration reaches some defined threshold thereby fixing the duration of interconnected stage. On the other hand, the duration of the remaining stages is fixed by recovery and regeneration protocol established in batch experiments. The set of operations performed in the multi-column chromatography may not be considered as a direct extension of the batch chromatography due to the interconnections between the multiple columns. Operating conditions such as superficial velocities, salt concentration or pH maintained in mobile phase during the operations such as the load operation, the wash operation, and the elute operation may be considered as additional decision variables rather than adapting the same from the batch operations. Finding the operating conditions that result in optimal performance of the set of chromatography operations using the MCC configuration, is considered as an MCC process optimization. Traditionally, exploratory experiments have been performed to identify favorable operating conditions resulting in sub-optimal performance, since the number of experiments may only be finite due to time and resource constraints. Conventional model-driven optimization approaches for finding the favorable operating conditions are limited. Conventional mathematical model-based approaches have been utilized as tools to explore the effect of the operating conditions and various design decisions on performance of the chromatography operations. However, the conventional optimization approaches that outline (i) a set of decision variables associated with the operating conditions to be maintained at each operation and (ii) characteristics of the multiple columns present in the MCC, are limited.

The present disclosure herein provides methods and systems that solve the technical problem of identifying the operational conditions that optimize the MCC process and the MCC configuration. A multi-objective optimization function defined with one or more decision variables associated with the operating conditions is considered to determine the optimal MCC configuration and hence the MCC process, while meeting the purification goals. The duration of each stage and the superficial velocities during the wash operation and the elution operation are considered as additional decision variables while determining the optimal MCC configuration of the MCC process.

In the context of the present disclosure, the chromatographic operation (s) or simply the operation (s) are simultaneously used, which refer to the set of chromatography operations including a load operation, a wash operation, a elute operation and an equilibration operation. In the present disclosure, the desired product to be captured from the feed for example the clarified cell culture fluid, is considered as for example monoclonal antibodies. However, the scope of the present disclosure is not limited to the considered example.

Referring now to the drawings, and more particularly to FIG. 1 through FIG. 6, where similar reference characters denote corresponding features consistently throughout the figures, there are shown preferred embodiments and these embodiments are described in the context of the following exemplary systems and/or methods.

FIG. 1 is an exemplary block diagram of a system 100 for determining an optimum multi-column chromatography (MCC) configuration of the MCC process, in accordance with some embodiments of the present disclosure. In an embodiment, the system 100 includes or is otherwise in communication with one or more hardware processors 104, communication interface device(s) or input/output (I/O) interface(s) 106, and one or more data storage devices or memory 102 operatively coupled to the one or more hardware processors 104. The one or more hardware processors 104, the memory 102, and the I/O interface(s) 106 may be coupled to a system bus 108 or a similar mechanism.

The I/O interface(s) 106 may include a variety of software and hardware interfaces, for example, a web interface, a graphical user interface, and the like. The I/O interface(s) 106 may include a variety of software and hardware interfaces, for example, interfaces for peripheral device(s), such as a keyboard, a mouse, an external memory, a plurality of sensor devices, a printer and the like. Further, the I/O interface(s) 106 may enable the system 100 to communicate with other devices, such as web servers and external databases.

The I/O interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface(s) 106 may include one or more ports for connecting a number of computing systems with one another or to another server computer. Further, the I/O interface(s) 106 may include one or more ports for connecting a number of devices to one another or to another server.

The one or more hardware processors 104 may be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In the context of the present disclosure, the expressions 'processors' and 'hardware processors' may be used interchangeably. In an embodiment, the system 100 can be implemented in a variety of computing systems, such as laptop computers, portable computer, notebooks, hand-held devices, workstations, mainframe computers, servers, a network cloud and the like.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 102 includes a plurality of modules 102a and a repository 102b for storing data processed, received, and generated by one or more of the plurality of modules 102a. The plurality of modules 102a may include routines, programs, objects, components, data structures, and so on, which perform particular tasks or implement particular abstract data types.

The plurality of modules 102a may include programs or computer-readable instructions or coded instructions that supplement applications or functions performed by the system 100. The plurality of modules 102a may also be used as, signal processor(s), state machine(s), logic circuitries, and/ or any other device or component that manipulates signals based on operational instructions. Further, the plurality of modules 102a can be used by hardware, by computer-readable instructions executed by the one or more hardware processors 104, or by a combination thereof. In an embodiment, the plurality of modules 102a can include various sub-modules (not shown in FIG. 1). Further, the memory 102 may include information pertaining to input(s)/output(s) of each step performed by the processor(s) 104 of the system 100 and methods of the present disclosure.

The repository 102b may include a database or a data engine. Further, the repository 102b amongst other things, may serve as a database or includes a plurality of databases for storing the data that is processed, received, or generated as a result of the execution of the plurality of modules 102a. Although the repository 102a is shown internal to the system 100, it will be noted that, in alternate embodiments, the repository 102b can also be implemented external to the system 100, where the repository 102b may be stored within an external database (not shown in FIG. 1) communicatively coupled to the system 100. The data contained within such external database may be periodically updated. For example, new data may be added into the external database and/or existing data may be modified and/or non-useful data may be deleted from the external database. In one example, the data may be stored in an external system, such as a Lightweight Directory Access Protocol (LDAP) directory and a Relational Database Management System (RDBMS). In another embodiment, the data stored in the repository 102b may be distributed between the system 100 and the external database.

Figure 2:
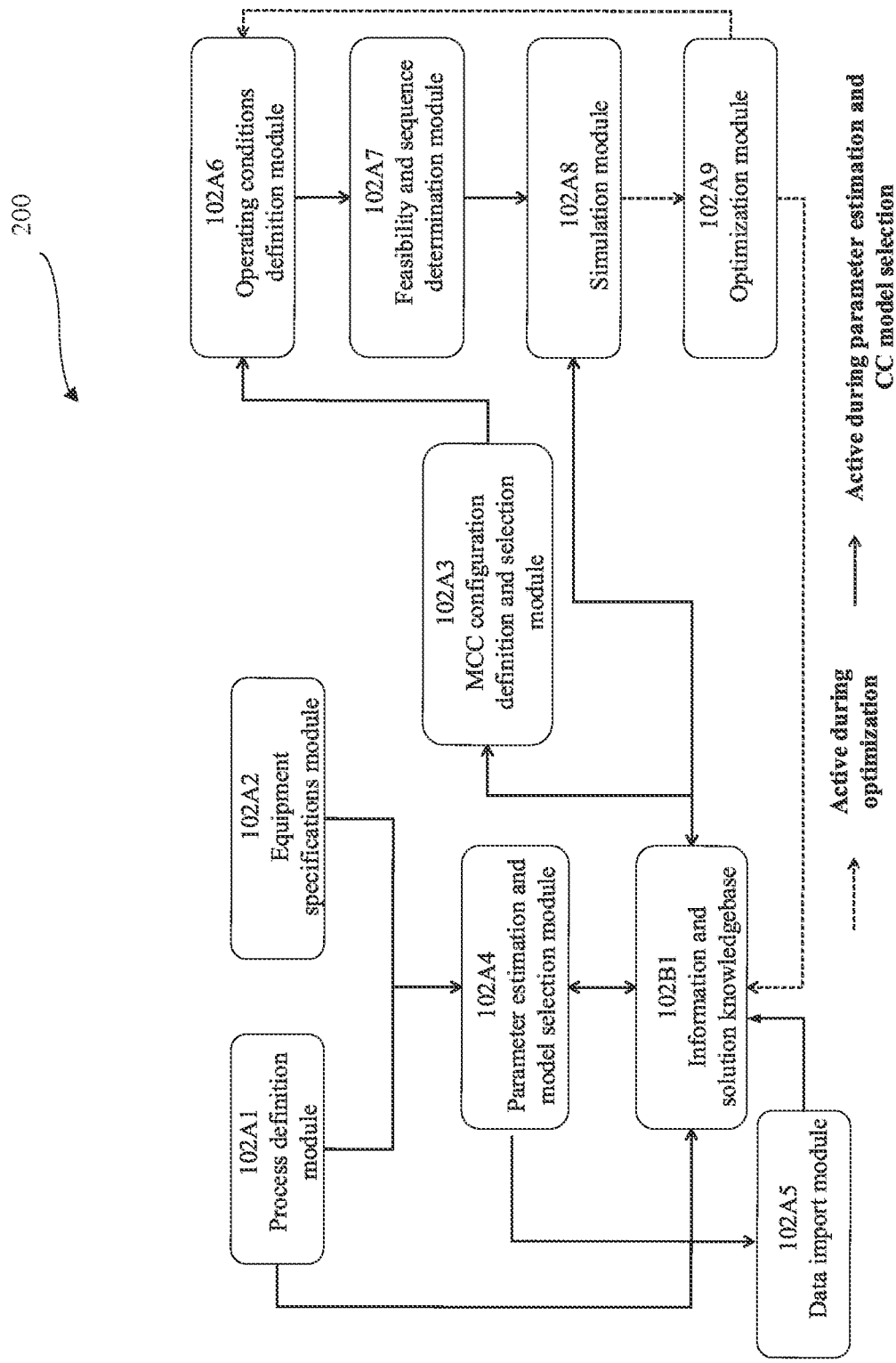
FIG. 2 is an exemplary block diagram illustrating modules of a system of FIG. 1 for determining an optimum multi-column chromatography (MCC) configuration of an MCC process, in accordance with some embodiments of the present disclosure.
Figure 3:
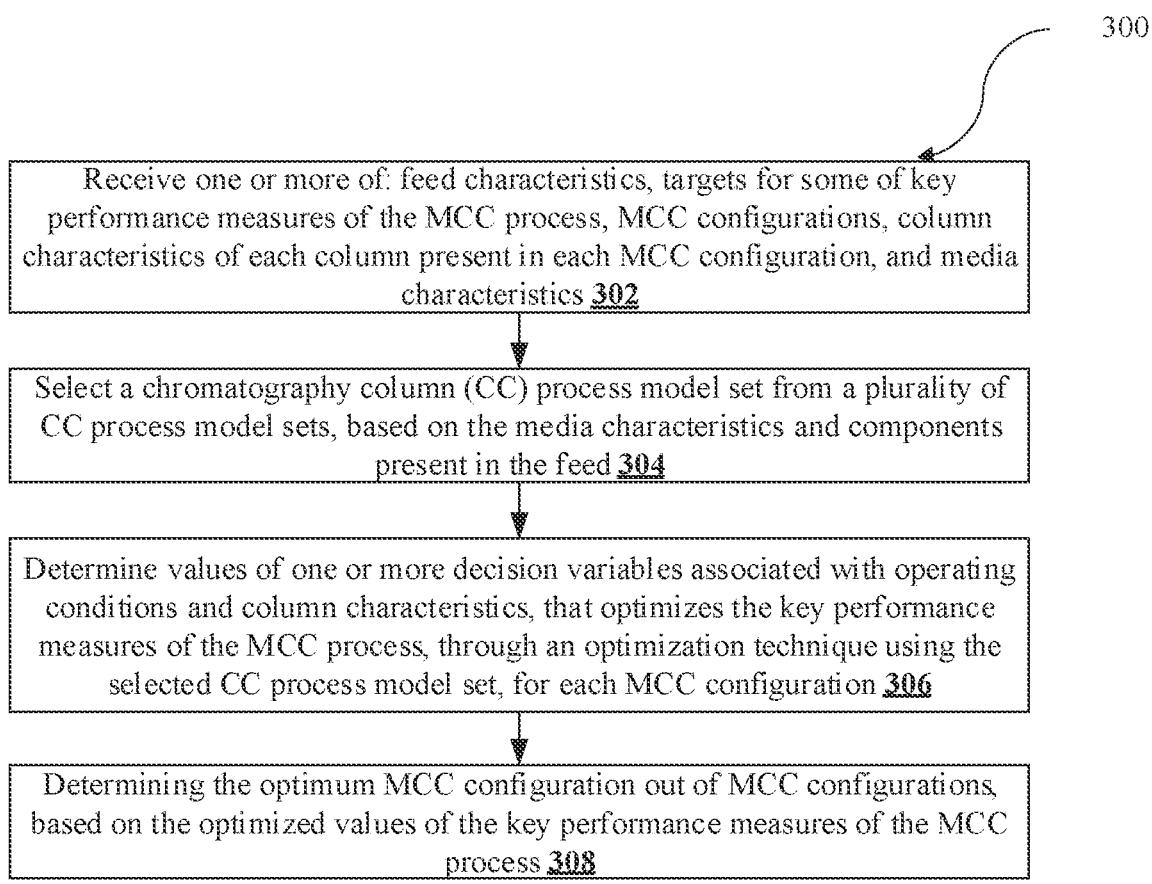
FIG. 3 illustrates an exemplary flow diagram of a processor-implemented method for determining the optimum multi-column chromatography (MCC) configuration of the MCC process, in accordance with some embodiments of the present disclosure.

Referring collectively to FIG. 2 and FIG. 3, components and functionalities of the system 100 are described in accordance with an example embodiment of the present disclosure. For example, FIG. 2 is an exemplary block diagram illustrating modules of the system 100 of FIG. 1 for determining the optimum multi-column chromatography (MCC) configuration of the MCC process, according to some embodiments of the present disclosure. As shown in FIG. 2, the modules include a process definition module 102a1, an equipment specifications module 102a2, an MCC configuration definition and selection module 102a3, a parameter estimation and model selection module 102a4, a data import module 102a5, an operating conditions definition module 102a6, a feasibility and sequence determination module 102a7, a simulation module 102a8, an optimization module 102a9, and an information and solution knowledgebase 102b1. In an embodiment, the modules of FIG. 2 except the information and solution knowledgebase 102b1, may be stored in the plurality of modules 102a comprised in the memory 102 of the system 100. The information and solution knowledgebase 102b1 may be stored in the repository 102b comprised in the memory 102 of the system 100.

FIG. 3 illustrates an exemplary flow diagram of a processor-implemented method 300 for determining the optimum multi-column chromatography (MCC) configuration of the MCC process, in accordance with some embodiments of the present disclosure. Although steps of the method 300 including process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any practical order. Further, some steps may be performed simultaneously, or some steps may be performed alone or independently.

At step 302 of the method 300, the one or more hardware processors 104 of the system 100 are configured to receive one or more of: feed characteristics, targets for some of one or more key performance measures of the MCC process, one or more MCC configurations of the MCC process, one or more column characteristics of each column of one or more columns present in each MCC configuration, and media characteristics of one or more chromatography media for use in each column of one or more columns.

The feed characteristics defines the characteristics of the feed that includes the antibodies which are to be captured using the MCC process. The feed characteristics includes a feed composition, a feed flow rate and its physical properties including a pressure, a temperature, a density and a pH value. The feed composition includes one or more components that are present in the feed along with their proportion and the component (product) to be captured, for example the antibodies. In an embodiment, the feed characteristics may be received through the process definition module 102a1, from a user. The targets for some of one or more key performance measures of the MCC process define minimum desired limits for some of the one or more key performance measures. In an embodiment, the one or more key performance measures include a productivity, a capacity utilization, a product yield, and a product purity. The one or more key performance measures are associated with the product to be captured from the feed. The product purity is one of purification goals, that indicates the purity of the product (antibodies) that is to be maintained during the capture process. The product yield indicates the yield of the product to be captured. In an embodiment, the targets for some of one or more key performance measures of the MCC process may be received through the process definition module 102a1, from the user.

Each MCC configuration of the one or more MCC configurations defines the number of columns along with connections between each column, where the MCC configuration is to be used for performing MCC process to capture the antibodies from the feed. The MCC process defines number of stages to be performed, a sequence of the stages, the set of chromatography operations to be performed in each stage, number of sub-operations that may be present in each chromatography operation, operating conditions for each chromatography operation and the associated sub-operations. In an embodiment, the one or more MCC configurations may be the MCC configurations that are already available in the market. In another embodiment, the one or more MCC configurations may be the MCC configurations that are defined by the user. In further embodiment, the one or more MCC configurations may be a combination of MCC configurations that are already available in the market as well as the MCC configurations that are defined by the user. In an embodiment, the one or more MCC configurations of the MCC process may be received through the MCC configuration definition and selection module 102a3, from the user.

The one or more column characteristics define the characteristics of each column of the one or more columns that are present in each MCC configuration. The one or more column characteristics of each column include a column length, a cross-sectional area of the column and a column porosity. One or more chromatography media is used in each column for capturing the antibodies. Characteristics of each chromatography media of the one or more chromatography media, include a particle size of resin, a particle porosity, a particle density, and a static binding capacity. In an embodiment, the one or more column characteristics and the one or more chromatography media may be received through the equipment specifications module 102a2, from the user.

At step 304 of the method 300, the one or more hardware processors 104 of the system 100 are configured to select a chromatography column (CC) process model set from a plurality of CC process model sets. The CC process model set defines a set of models and their associated parameters for performing the MCC process. Each CC process model set comprises (i) a mobile phase mass transfer model and associated mobile phase model parameter (ii) a stationary phase mass transfer model and associated stationary phase parameters, and (iii) an adsorption-desorption model and associated adsorption-desorption parameters. In an embodiment, the associated mobile phase model parameter includes a column dispersion coefficient. The associated stationary phase parameters include an effective diffusion coefficient in pores and an interfacial mass transfer coefficient. The associated adsorption-desorption parameters include an adsorption rate constant and a desorption rate constant.

The chromatography column (CC) process model set from the plurality of CC process model sets, is selected based on the media characteristics of the one or more chromatography media for use in each column of the one or more columns and one or more components present in the feed, that are received at step 302 of the method 300. In an embodiment, the plurality of CC process model sets may be stored in a knowledge base 102b2 (not shown in FIG. 1) that is present in the repository 102b of the system 100. In an embodiment, each CC process model set may include a transport dispersion model, an equilibrium dispersion model and a general rate model.

Figure 4:
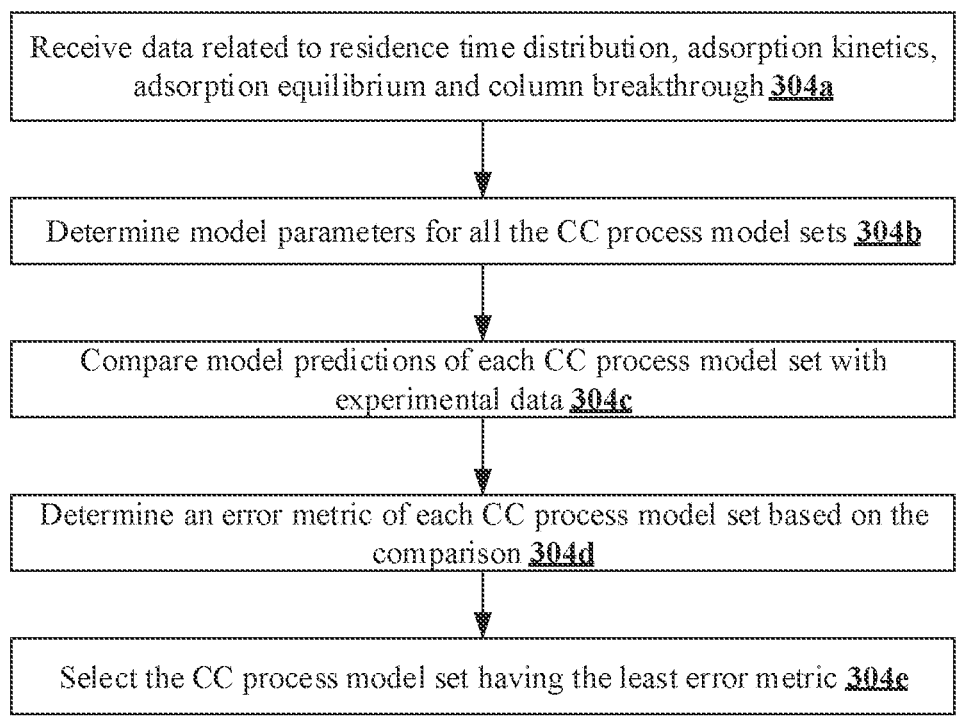
FIG. 4 illustrates an exemplary flow diagram for selecting a chromatography column (CC) process model set, from a plurality of CC process model sets, in accordance with some embodiments of the present disclosure.

In an embodiment, the CC process model set is selected from the plurality of CC process model sets, through the parameter estimation and model selection module 102a4. FIG. 4 illustrates an exemplary flow diagram for selecting the chromatography column (CC) process model set, from the plurality of CC process model sets, in accordance with some embodiments of the present disclosure. At step 304a of FIG. 4, a set of data including residence time distribution data, adsorption kinetics data, adsorption equilibrium data and column breakthrough data, is received. In an embodiment, the set of data may be received through the data import module 102a5. The set of data may be obtained from batch chromatography experiments that are carried out based on the media characteristics of the one or more chromatography media for use in each column of the one or more columns and one or more components present in the feed, using a simulation technique configured in a simulation module 102a8. In an embodiment, the set of data may be received from the data import module 102a5 when the set of data is not present in the information and solution knowledgebase 102b1. The set of data that is received from the data import module 102a5, is stored in the information and solution knowledgebase 102b1 for future use. At step 304b of FIG. 4, CC model parameters for each CC process model set are determined. In an embodiment, the CC model parameters includes associated mobile phase model parameter, associated stationary phase parameters and associated adsorption-desorption parameters. The CC model parameters for each CC process model set are determined from the set of data received at step 304a of FIG. 4.

At step 304c of FIG. 4, model predictions (obtained from the associated determined CC model parameters) are compared with experimental data. At step 304d of FIG. 4 an error metric for each CC process model set are determined based on the comparison between the model predictions and the experimental data. by comparing. In an embodiment, the error metric for each CC process model set is determined by using one of an error metric models selected from a group consists of: a mean square error model, a mean absolute error model, and so on. The error metric determines a percent relative error for each CC process model set. At step 304e of FIG. 4, the CC process model set is selected that is having a least error metric (the percentage relative error). In an embodiment, the CC process model set having the determined error metric (the percentage relative error) less than a predefined threshold error may be selected. In an embodiment, the predefined threshold error may be 0.3%. In an embodiment, the determined error metric for each CC process model set (performance metrics associated with the plurality of CC process model sets) is stored in the knowledge base 102b2 for future use.

At step 306 of the method 300, the one or more hardware processors 104 of the system 100 are configured to determine values of one or more decision variables that optimize the one or more key performance measures of the MCC process for each MCC configuration of the one or more MCC configurations, using the selected CC process model set that is obtained at step 304 of the method 300. The values of the one or more decision variables are determined to obtain the optimized values of the one or more key performance measures for each MCC configuration, by using an optimization technique configured in the optimization module 102a9. In an embodiment, a particle swarm optimization technique is explained in the disclosure as an exemplary optimization technique, however the scope of the present disclosure is not limited to the particle swarm optimization technique. A skilled person in the art may exercise any similar technique in place of the particle swarm optimization technique.

The one or more decision variables are associated with operating conditions to be maintained at each chromatographic operation of the set of chromatographic operations during the MCC process and the one or more column characteristics of each column of one or more columns present in the associated MCC configuration. The one or more decision variables associated with the operating conditions that are to be maintained at each operation include duration of each stage of MCC process, the pH value, a salt concentration, and a superficial velocity of process stream. In an embodiment, some of the one or more decision variables associated with the operating conditions that may be fixed by the user may be received through the operating conditions definition module 102a6.

Figure 5:
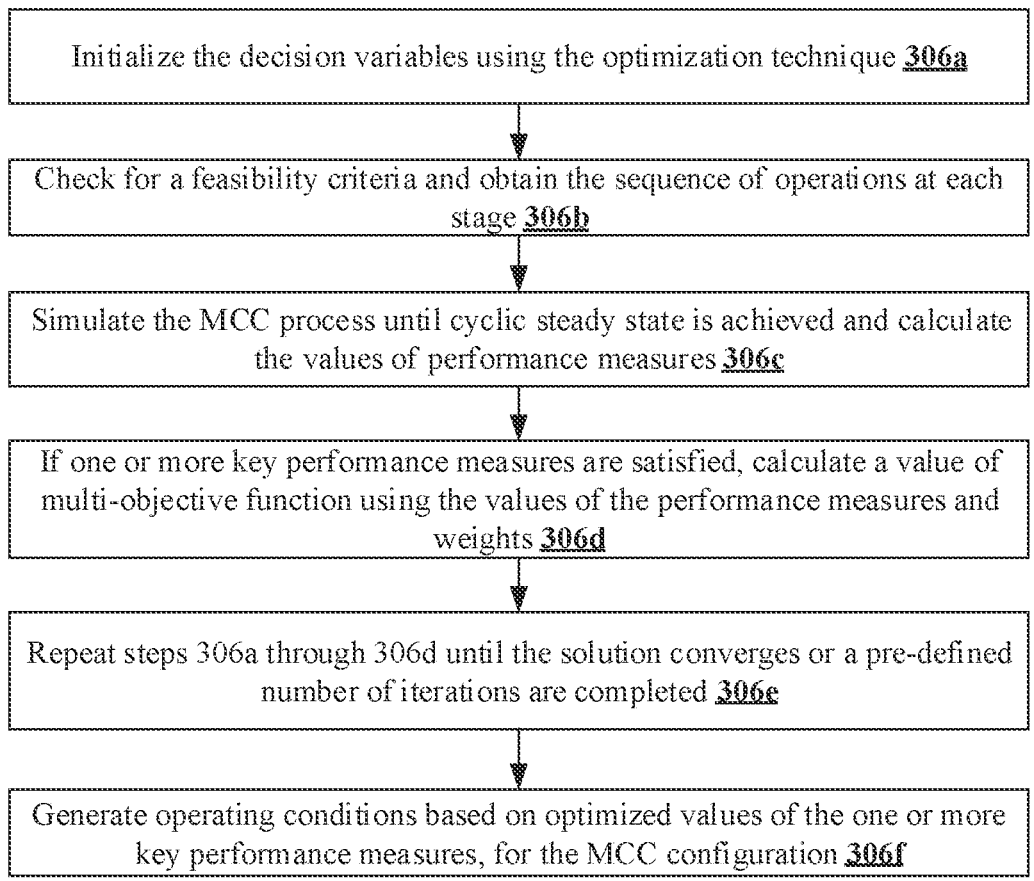
FIG. 5 illustrates an exemplary flow diagram for determining one or more decision variables that optimizes the one or more key performance measures of the MCC process, for each MCC configuration, in accordance with some embodiments of the present disclosure.

FIG. 5 illustrates an exemplary flow diagram for determining the one or more decision variables that optimizes the one or more key performance measures of the MCC process, for each MCC configuration, in accordance with some embodiments of the present disclosure. The values of one or more decision variables that optimizes the one or more key performance measures of the MCC process to obtain optimized values of the one or more key performance measures, for each MCC configuration, are determined as mentioned in FIG. 5 through steps 306a to 306f, by using the selected CC process model set that is obtained at step 304 of the method 300.

At step 306a, initial values of the one or more decision variables are generated using the optimization technique. The initial values of the one or more decision variables include an initial value for each decision variable of the one or more decision variables. The one or more decision variables are referred as particles by the particle swarm optimization technique where S being a number of particles indicating a number of the one or more decision variables. The initial value of each decision variable of the one or more decision variables is generated based on below equation:

$$\text{Initial value} = \text{lower limit value} + (\text{upper limit value} - \text{lower limit value}) * U(0,1) \qquad (1)$$

where the lower limited value and the upper limit values are defined by the user and U is a predefined constant which ranges between '0' and '1'.

At step 306b, sequence of chromatographic operations at each stage of the MCC process and a duration of each sequence of chromatographic operations at each stage of the MCC process, are obtained, if the initial values of the one or more decision variables generated at step 306a, satisfies a feasibility criteria. In an embodiment, the feasibility criteria is associated with completion of regeneration protocol during a column switch and completion of predefined number of wash volumes.

Figure 6:
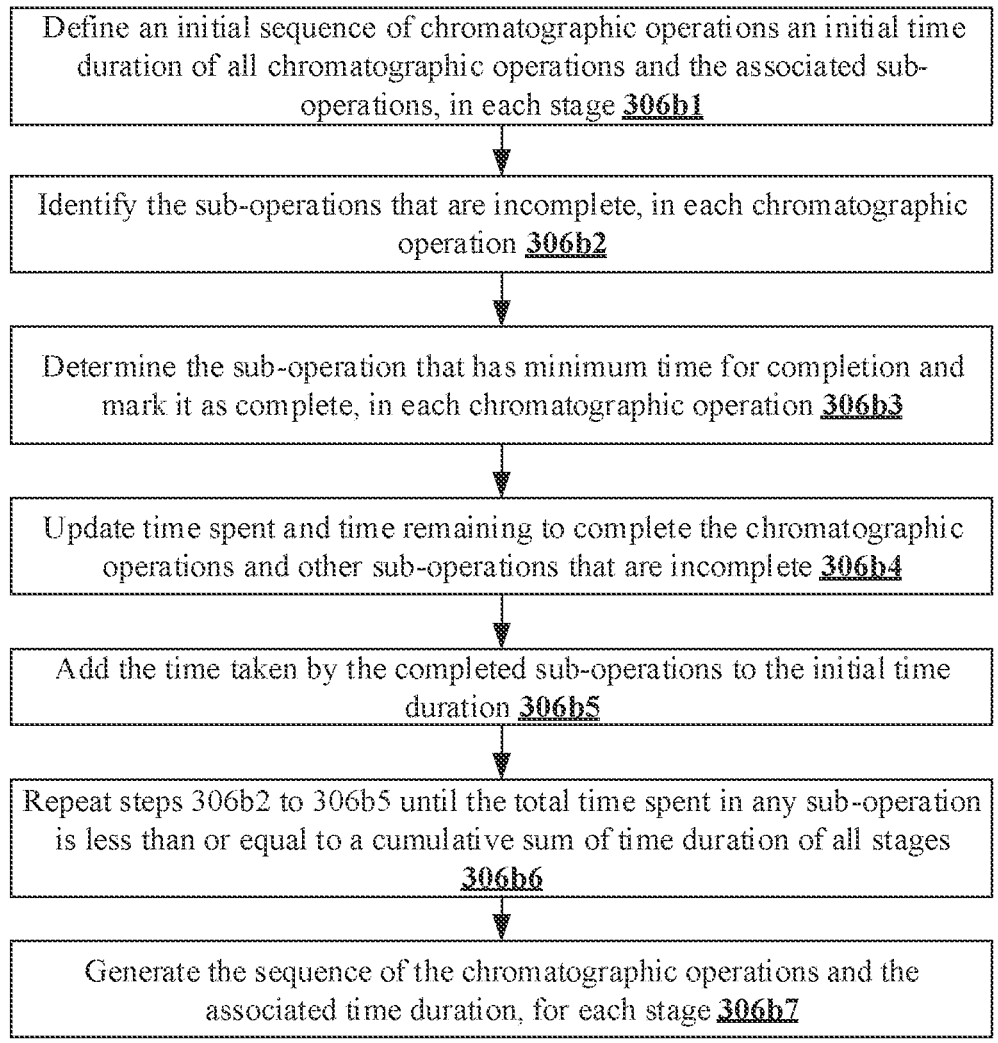
FIG. 6 illustrates an exemplary flow diagram for obtaining a sequence of chromatographic operations at each stage and a time duration of chromatographic operations at each stage of the MCC process, in accordance with some embodiments of the present disclosure.

FIG. 6 illustrates an exemplary flow diagram for obtaining a sequence of chromatographic operations at each stage and the time duration of chromatographic operations, at each stage of the MCC process, in accordance with some embodiments of the present disclosure. In an embodiment, the sequence of chromatographic operations at each stage and the duration of chromatographic operations, at each stage of the MCC process are obtained as mentioned in FIG. 6 through steps 306b1 to 306b7. In an embodiment, the number of stages is predefined and may be defined by user. The number of stages indicate the unique number of points during a single switch of the chromatography column present in the MCC configuration.

At step 306b1, an initial sequence of chromatographic operations and an initial time duration of each chromatographic operation present in the initial sequence of chromatographic operations, and the initial time duration for each sub-operation of one more sub-operations that may present in each chromatographic operation, at each stage are defined by the user. For example, the initial time duration may be '0' sec/minutes. As step 306b2, if total time spent in any sub-operation is less than or equal to the cumulative sum of time duration of the stages, then the one or more sub-operations corresponding to each chromatographic operation, that are incomplete and to be performed simultaneously in the associated MCC configuration, are identified. At step 306b3, the sub-operation having a shortest remaining time duration, among the one or more sub-operations identified at step 306b2 is determined. The determined sub-operation having the shortest remaining time duration is marked as complete.

At step 306b4, the one or more sub-operations and the one or more chromatographic operations that are completed are captured and time duration spent for each completed sub-operations and the chromatographic operations are updated and the remaining time duration for completing the incomplete sub-operations and the chromatographic operations are also updated, to obtain a successive sequence of chromatographic operations and sub-operations at each stage. At step 306b5, the successive time duration of the sequence of chromatographic operations is calculated by adding the time taken by the sub-operations and the chromatographic operations, that are completed, based on the start time and end time, to the initial duration. The end time is estimated after considering the time taken to reach the cyclic steady state. For example, the end time may be calculated by multiplying the time taken to reach cyclic steady state with the duration of each cycle. The duration of each cycle is calculated my multiplying the number of columns present in the associated MCC configuration with a switch time. The switch time is calculated by adding the duration of each stage of the one or more stages.

At step 306b6, repeating the steps 306b1 through 306b5, by taking the successive sequence of chromatographic operations obtained at step 306b4 as the initial sequence of operations and taking the successive time duration of the sequence of chromatographic operations and sub-operations, obtained at step 306b5 as the initial time duration of the sequence of chromatographic operations and sub-operations, until the one or more chromatographic operations and the one or more sub-operations present in each chromatographic operations, at each stage, are completed. At step 306b7, the successive sequence of chromatographic operations and the successive time duration of the sequence of chromatographic operations and sub-operations, obtained, after performing the step 306b6 and after all the stages are completed, are considered as the sequence of chromatographic operations at each stage and the time duration of the sequence of chromatographic operations and sub-operations, for the corresponding stage, respectively.

At step 306c, the one or more key performance measures of the MCC process are calculated by simulating the MCC process using the selected CC model set for the obtained sequences of chromatographic operations and the time duration of each sequence, for each stage of the one or more stages, until a cyclic steady state (CSS) of the MCC configuration is achieved. This may be achieved through the simulation module 102a8.

In simulating the MCC process, inlet boundary condition for each of the column of the associated MCC configuration takes into account, the change in the operating conditions associated with each chromatographic operation and interconnected nature of column operations. In case of interconnected feed or interconnected wash operation, concentration at exit of the upstream column, $c(t,z=L)$, is set as inlet concentration $c_{in}$, according to Danckwerts boundary condition, for the downstream column. During the loading operation, for the column receiving the feed, the inlet concentration $c_{in}$ is set equal to $c_{feed}$, concentration of monoclonal antibodies mAb. While simulating the wash and elute operations, the inlet concentration $c_{in}$ is set equal to zero since monoclonal antibodies mAb is absent in the incoming buffer stream.

Furthermore, to maintain continuity of concentration profile within a given chromatography column while moving from one set of chromatographic operation to other including column switching, the previously obtained concentration profile was used as initial condition for the next stage of chromatography operation. The number of partial differential equations (PDEs) to be solved are equal to the number of columns present in the MCC configuration. Only a single adsorbing component is assumed in these simulations. A finite volume approach may be applied to discretize terms with spatial dependence in the PDE and thus transform the PDEs to ordinary differential equations (ODEs). In particular, first-order upwind scheme is used to discretize the convective term, while central difference scheme is used to discretize axial dispersion term. The transformed equations may be expressed as the ordinary differential equations with number of ODEs equal to number of control volumes used for discretizing a single PDE times number of columns in the MCC configuration which works out to be $N_{cv} \times N_{col}$.

$$\frac{dc_j^i}{dt} = -\frac{v(c_{j+1}^i - c_j^i)}{\Delta z_j^{cv}} + \frac{D_L(c_{j+1}^i - 2c_j^i + c_{j-1}^i)}{(\Delta z_j^{cv})^2} - \frac{1-\varepsilon}{\varepsilon}\frac{dq_j^i}{dt} \quad (2)$$

$$\frac{dq_j^i}{dt} = k_m(q*(c_j^i) - q_j^i) \quad (3)$$

where $j \in \{1, 2, \ldots N_{cv}\}$ represents a control volume while $\Delta z_j^{cv}$ represents its size. The index $i \in \{1, 2, \ldots N_{col}\}$ represents chromatography column in the MCC configuration. In an embodiment, a backward differentiation formula method may be used to transform the equations from PDEs to ODE form. For the first control volume that encloses boundary at $z=0$, concentration at the leftmost boundary, $c_{w,j=0}$, can be expressed in terms of $c_{j=0}$, concentration at the center of control volume, by discretizing diffusive flux according to the Danckwerts boundary condition as mentioned below:

$$c_w = \frac{c_{in}}{1+K} + \frac{Kc_{j=0}}{1+K} \quad (4)$$

where $$K = \frac{D_L}{u\Delta z_{j=0}^w},$$

with $\Delta z_{j=0}^w$ being the distance between center of the first control volume and its west facing boundary. The transport equation for the last cell was discretized by considering zero diffusive flux at its east facing boundary to account for fully developed concentration profile.

At the beginning of chromatography operations, (k=0), k being cycle number, one of the column receives the feed, while the other columns are idle. Cyclic steady state is achieved when there is no further change in internal concentration profile of adsorbable component in each of columns. It may be typically achieved after few cycles of chromatographic operations are conducted. In an embodiment, a time integral of concentration of antibodies mAb at the outlet of each column, representative of the mass flow, during each of the chromatographic operation is numerically calculated. If relative change in this integral between two subsequent cycles, $rel_{CSS}^{i+1|i}$, is found to be less than a predefined threshold, it is inferred that the chromatography operations have reached cyclic steady state as stated in the below equation:

$$ref_{CSS}^{i+1|i} = \left( \frac{\int_0^{\Delta t} c^{i+1} dt}{\int_0^{\Delta t} c^i dt} - 1 \right) \quad (5)$$

After attainment of cyclic steady state, one or more key performance measures of the MCC process are calculated. The product yield is defined as the ratio of total amount of product collected during elution to the total amount of the feed delivered to the column. The product yield is calculated as the below equation:

$$\text{Product yield} = \frac{\int_0^{t_{elution}} c_{mAb}(t, z=L) u_s^{elution} A_{col} dt}{\sum_{i=1}^{n_{loadstages}} c_f^i u_s^{feed} A_{col} \Delta T^i} \quad (6)$$

where, $t_{elution}$ is duration of elution operation, $u_s^{elution}$ is the superficial velocity maintained in the column that is being eluted, $A_{col}$ is cross-sectional area of the column, $n_{load_{stages}}$ is the number of loading operations, $c_f^i$, is the concentration of mAb in the feed stream during the stage i, $u_s^{feed}$ is superficial velocity maintained in the column during loading, and $\Delta T^i$ is the duration of stage i.

The productivity is an amount of antibodies mAb collected in elution stream per unit column volume during a complete cycle of chromatography operation and is calculated as mentioned in the below equation:

$$\text{Productivity} = \frac{\int_0^{t_{elution}} c_{mAb}(t, z=L) u_s^{elution} A_{col} dt}{t_{cycle} V_{col} (1 - \varepsilon_{col})} \quad (7)$$

where, $t_{cycle}$ is cycle time defined as total duration after which the column configuration returns to its initial state, and can be worked out as $t_{cycle} = N_{col} \Sigma_{i=1}^{N} \Delta T^i$ and $\varepsilon_{col}$ is the column porosity.

The capacity utilization is an amount of antibodies mAb produced per unit adsorption capacity of the column.

$$\text{Capacity utilization} = \frac{\int_0^{t_{elution}} c_{mAb}(t, z=L) u_s^{elution} A_{col} dt}{q_{feed}^* V_{col} (1 - \varepsilon_{col})} \quad (8)$$

where, $q_{feed}^*$, represents concentration of antibodies mAb in solid state that is in equilibrium with concentration of the feed in liquid state $c_f$. This may be estimated using modified Langmuir isotherm with pH maintained during the load operation.

The integrals appearing in the above equations are calculated numerically using Simpson's rule. The values of the performance measures are corrected such that these are maintained within their physical limits. In particular, the product yield and the capacity utilization cannot be greater than 1.

In an embodiment, the purity may be defined as the concentration of antibodies divided by the total concentration of different components present in the elute stream.

At step 306d, a value of a multi-objective function is calculated, if some of the one or more key performance measures determined at step 306c are satisfied against the targets for the corresponding one or more key performance measures of the MCC process received at step 302. The multi-objective function is defined as a weighted sum of the one or more key performance measures. In an embodiment, the multi-objective function is mentioned in the below equation:

Multi-objective function=$-1*(a*$product yield+
$b*$productivity+$c*$capacity utilization) (9)

where a, b, c are predefined weights. '$-1$' in the multi-objective function is included to get a positive value. In an embodiment, the predefined weights may be a=0.33, b=0.33 and C=0.33, where a+b+c=1.

At step 306e, a successive value for each decision variable of the one or more decision variables, are generated using the optimization technique, based on the calculated value of the multi-objective function, to obtain the successive values of the one or more decision variables. In an embodiment, the successive value for each decision variable of the one or more decision variables, is generated using the below mentioned equation:

Successive value=initial value+$c1*w*$(previous best
value-initial value)+$c1*w*$global best initial
value (10)

where c1 and w are predefined weights and for example, c1 may take a value from a range 1.5-1.7 and w may take a value from the range 0.7-0.8. The previous best value and the global best initial values are the values evaluated during the optimization at each iteration.

Also at step 306e, the steps 306b through 306e are repeated sequentially at each iteration, by considering the successive values of the one or more decision variables as the initial values, until either (i) a difference between the values of the multi-objective function for two successive iterations is less than a predefined threshold value (converges) or (ii) a predefined number of the iterations are performed. In an embodiment, the predefined number of the iterations may be 100. The values of the one or more decision variables obtained after completion of the step 306e are considered as the values of the one or more decision variables that optimizes the one or more key performance measures of the MCC process for the corresponding MCC configuration. At step 306f, the one or more decision variables associated with the operating conditions, that derive the optimized values of the one or more key performance measures of the MCC process, are obtained, for each MCC configuration.

At step 308 of the method 300, the one or more hardware processors 104 of the system 100 are configured to determine the optimum MCC configuration out of one or more MCC configurations, based on the associated optimized values of the one or more key performance measures of the MCC process. In an embodiment, the MCC configuration that gives the maximum value of the multi-objective function mentioned at step 306 of the method 300 based on the associated optimized values of the one or more key performance measures of the MCC process, is determined. The determined MCC configuration at step 308 of the method 300 along with (i) the chromatography column (CC) process model set selected at step 304 of the method 300 and (ii) the one or more decision variables are associated with operating conditions to be maintained at each chromatographic operation and sub-operation, and the one or more column characteristics of each column of one or more columns present in the MCC configuration, obtained at step 306 of the method 300, is considered for capturing the antibodies from the feed.

At step 310 of the method 300, the one or more hardware processors 104 of the system 100 are further configured to display the optimal MCC configuration and associated values of the one or more decision variables that are associated with the operating conditions, through a display unit. In an embodiment, the display unit may be connected to the system 100 via the I/O interface(s) 106.

In accordance with the present disclosure, the methods and systems, allows the user to define his/her own MCC configuration based on available resources of chromatographic columns. Determining the MCC configuration is achieved before the physical design of the MCC configuration, hence the amount of time and the material cost invested for designing the optimum MCC configuration is significantly decreased. The present disclosure evaluates different MCC configurations and determines the best MCC configuration along with corresponding optimal operating conditions at which it is to be operated at, given the processing requirements. Thus, it helps provide design of MCC configuration that meets purification targets while also optimizing the one or more key performance variables of interest.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims (when included in the specification), the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for determining an optimum multi-column chromatography (MCC) configuration of an MCC process, the method comprising the steps of:

receiving, via one or more hardware processors, one or more of: feed characteristics, targets for some of one or more key performance measures of the MCC process, one or more MCC configurations of the MCC process, one or more column characteristics of each column of one or more columns present in each MCC configuration, and media characteristics of one or more chromatography media for use in each column of one or more columns;

selecting, via the one or more hardware processors, a chromatography column (CC) process model set from a plurality of CC process model sets, based on the media characteristics of the one or more chromatography media for use in each column of the one or more columns and one or more components present in the feed, wherein each CC process model set comprises (i) a mobile phase mass transfer model and associated mobile phase model parameter (ii) a stationary phase mass transfer model and associated stationary phase parameters, and (iii) an adsorption-desorption model and associated adsorption-desorption parameters;

determining through an optimization technique, via the one or more hardware processors, values of one or more decision variables that optimizes the one or more key performance measures of the MCC process, to obtain optimized values of the one or more key performance measures, for each MCC configuration of the one or more MCC configurations, using the selected CC process model set, comprises:
(a) generating initial values of the one or more decision variables, using the optimization technique;
(b) obtaining sequence of chromatographic operations and a duration of each sequence of chromatographic operations at each stage of the MCC process, if the initial values of the one or more decision variables satisfies a feasibility criteria, wherein the feasibility criteria is associated with completion of regeneration protocol during a column switch and completion of predefined number of wash volumes;
(c) calculating the one or more key performance measures of the MCC process by simulating the MCC process using the selected CC model set for the obtained sequence of chromatographic operations and the duration of the sequence of chromatographic operations, at each stage, until a cyclic steady state (CSS) of the MCC configuration is achieved, wherein in simulating the MCC process, inlet boundary condition for each of the column of the associated MCC configuration takes into account, the change in the operating conditions associated with each chromatographic operation and interconnected nature of column operations,
wherein while simulating a wash operation and an elute operation, an inlet concentration $c_{in}$ is set equal to zero since monoclonal antibodies mAb is absent in the incoming buffer stream;
wherein the one or more decision variables are associated with operating conditions to be maintained at each chromatographic operation of a set of chromatographic operations to be performed at each stage, and the one or more column characteristics of each column of one or more columns present in the MCC configuration; and
determining, via the one or more hardware processors, the optimum MCC configuration out of one or more MCC configurations, based on the associated optimized values of the one or more key performance measures of the MCC process, wherein the optimum MCC configuration is determined before a physical design of the MCC configuration significantly decreasing an amount of time, a material cost invested for designing the optimum MCC configuration,
wherein the design of the MCC configuration meets purification targets and optimizing the one or more key performance measures.

2. The method of claim 1 further comprising displaying, via the one or more hardware processors, the optimal MCC configuration and along with the values of one or more decision variables associated with the optimized values of the one or more key performance measures through a display unit.

3. The method of claim 1, wherein selecting the CC process model set from the plurality of CC process model sets, comprises:
determining CC model parameters of each CC process model set, based on a set of source data comprising residence time distribution data, adsorption kinetics data, adsorption equilibrium data and column breakthrough data, wherein the CC model parameters of the associated CC process model set comprises the associated mobile phase model parameter, associated stationary phase parameters and associated adsorption-desorption parameters;
determining an error metric of each CC process model set, by comparing model predictions obtained from the determined CC model parameters with experimental data; and
selecting the CC process model set having a least error metric.

4. The method of claim 1, wherein determining the values of the one or more decision variables that optimizes the one or more key performance measures of the MCC process to obtain the optimized values of the one or more key performance measures, for each MCC configuration of the one or more MCC configurations, further comprises:
(d) calculating a value of a multi-objective function defined as a weighted sum of some of the one or more key performance measures;
(e) generating successive values of the one or more decision variables, using the optimization technique, based on the calculated value of the multi-objective function;
(f) repeating steps (a) through (e), at each iteration, by considering the successive values of the one or more decision variables as the initial values, until either (i) a difference between the values of the multi-objective function for two successive iterations is less than a predefined threshold value or (ii) a predefined number of the iterations are performed, to determine the values of the one or more decision variables that optimizes the one or more key performance measures of the MCC process; and
(g) obtaining the optimized values of the one or more key performance measures of the MCC process, based on the values of the one or more decision variables.

5. The method of claim 1, wherein the feed characteristics comprises of a feed composition comprising the one or more components, a feed flow rate and physical properties comprising a pressure, a temperature, a density and a pH value, the one or more key performance measures of the MCC process comprises a productivity, a capacity utilization, a product yield, and a product purity, the one or more column characteristics of each column comprises of a column length, a cross-sectional area of the column and a column porosity, and the characteristics of each chromatography media comprises of a particle size of resin, a particle porosity, a particle density and a static binding capacity.

6. The method of claim 1, wherein the associated mobile phase model parameter comprises a column dispersion coefficient, the associated stationary phase parameters comprises an effective diffusion coefficient in pores and an interfacial mass transfer coefficient, and the associated adsorption-desorption parameters comprises an adsorption rate constant and a desorption rate constant.

7. The method of claim 1, wherein the one or more decision variables associated with the operating conditions comprises a duration of each stage of MCC process, a pH value, a salt concentration, and a superficial velocity of process stream.

8. A system for determining an optimum multi-column chromatography (MCC) configuration of an MCC process, the system comprising:
a memory storing instructions;
one or more Input/Output (I/O) interfaces; and one or more hardware processors coupled to the memory via the one or more I/O interfaces, wherein the one or more hardware processors are configured by the instructions to:
receive or more of: feed characteristics, targets for some of one or more key performance measures of the MCC process, one or more MCC configurations of the MCC process, one or more column characteristics of each column of one or more columns present in each MCC configuration, and media characteristics of one or more chromatography media for use in each column of one or more columns;
select a chromatography column (CC) process model set from a plurality of CC process model sets, based on the media characteristics of the one or more chromatography media for use in each column of the one or more columns and one or more components present in the feed, wherein each CC process model set comprises (i) a mobile phase mass transfer model and associated mobile phase model parameter (ii) a stationary phase mass transfer model and associated stationary phase parameters, and (iii) an adsorption-desorption model and associated adsorption-desorption parameters;
determine through an optimization technique, values of one or more decision variables that optimizes the one or more key performance measures of the MCC process, to obtain optimized values of the one or more key performance measures, for each MCC configuration of the one or more MCC configurations, using the selected CC process model set, by:
(a) generating initial values of the one or more decision variables, using the optimization technique;
(b) obtaining sequence of chromatographic operations and a duration of each sequence of chromatographic operations at each stage of the MCC process, if the initial values of the one or more decision variables satisfies a feasibility criteria, wherein the feasibility criteria is associated with completion of regeneration protocol during a column switch and completion of predefined number of wash volumes;
(c) calculating the one or more key performance measures of the MCC process by simulating the MCC process using the selected CC model set for the obtained sequence of chromatographic operations and the duration of the sequence of chromatographic operations, at each stage, until a cyclic steady state (CSS) of the MCC configuration is achieved, wherein in simulating the MCC process, inlet boundary condition for each of the column of the associated MCC configuration takes into account, the change in the operating conditions associated with each chromatographic operation and interconnected nature of column operations,
wherein while simulating a wash operation and an elute operation, an inlet concentration $c_{in}$ is set equal to zero since monoclonal antibodies mAb is absent in the incoming buffer stream;
wherein the one or more decision variables are associated with operating conditions to be maintained at each chromatographic operation of a set of chromatographic operations to be performed at each stage, and the one or more column characteristics of each column of one or more columns present in the MCC configuration; and
determine the optimum MCC configuration out of one or more MCC configurations, based on the associated optimized values of the one or more key performance measures of the MCC process, wherein the optimum MCC configuration is determined before a physical design of the MCC configuration significantly decreasing an amount of time, a material cost invested for designing the optimum MCC configuration,
wherein the design of the MCC configuration meets purification targets and optimizing the one or more key performance measures.

9. The system of claim 8, wherein the one or more hardware processors are further configured to display the optimal MCC configuration and along with the values of one or more decision variables associated with the optimized values of the one or more key performance measures through a display unit connected to the system via the I/O interface(s).

10. The system of claim 8, wherein the one or more hardware processors are further configured to select the CC process model set from the plurality of CC process model sets, by:
determining CC model parameters of each CC process model set, based on a set of source data comprising residence time distribution data, adsorption kinetics data, adsorption equilibrium data and column breakthrough data, wherein the CC model parameters of the associated CC process model set comprises the associated mobile phase model parameter, associated stationary phase parameters and associated adsorption-desorption parameters;
determining an error metric of each CC process model set, by comparing model predictions obtained from the determined CC model parameters with experimental data; and
selecting the CC process model set having a least error metric.

11. The system of claim 8, wherein the one or more hardware processors are further configured to determine the values of the one or more decision variables that optimizes the one or more key performance measures of the MCC process to obtain the optimized values of the one or more key performance measures, for each MCC configuration of the one or more MCC configurations, by:
(d) calculating a value of a multi-objective function defined as a weighted sum of some of the one or more key performance measures;
(e) generating successive values of the one or more decision variables, using the optimization technique, based on the calculated value of the multi-objective function;
(f) repeating steps (a) through (e), at each iteration, by considering the successive values of the one or more decision variables as the initial values, until either (i) a difference between the values of the multi-objective function for two successive iterations is less than a predefined threshold value or (ii) a predefined number of the iterations are performed, to determine the values of the one or more decision variables that optimizes the one or more key performance measures of the MCC process; and
(g) obtaining the optimized values of the one or more key performance measures of the MCC process, based on the values of the one or more decision variables.

12. The system of claim 8, wherein the feed characteristics comprises of a feed composition comprising the one or more components, a feed flow rate and physical properties comprising a pressure, a temperature, a density and a pH value, the one or more key performance measures of the MCC process comprises a productivity, a capacity utilization, a product yield, and a product purity, the one or more column characteristics of each column comprises of a column length, a cross-sectional area of the column and a column porosity, and the characteristics of each chromatography media comprises of a particle size of resin, a particle porosity, a particle density and a static binding capacity.

13. The system of claim 8, wherein the associated mobile phase model parameter comprises a column dispersion coefficient, the associated stationary phase parameters comprises an effective diffusion coefficient in pores and an interfacial mass transfer coefficient, and the associated adsorption-desorption parameters comprises a adsorption rate constant and a desorption rate constant.

14. The system of claim 8, wherein the one or more decision variables associated with the operating conditions comprises a duration of each stage of MCC process, a pH value, a salt concentration, and a superficial velocity of process stream.

15. A computer program product comprising a non-transitory computer readable medium having a computer readable program embodied therein, wherein the computer readable program, when executed on a computing device, causes the computing device to:
   receive or more of: feed characteristics, targets for some of one or more key performance measures of the MCC process, one or more MCC configurations of the MCC process, one or more column characteristics of each column of one or more columns present in each MCC configuration, and media characteristics of one or more chromatography media for use in each column of one or more columns;
   select a chromatography column (CC) process model set from a plurality of CC process model sets, based on the media characteristics of the one or more chromatography media for use in each column of the one or more columns and one or more components present in the feed, wherein each CC process model set comprises (i) a mobile phase mass transfer model and associated mobile phase model parameter (ii) a stationary phase mass transfer model and associated stationary phase parameters, and (iii) an adsorption-desorption model and associated adsorption-desorption parameters;
   determine through an optimization technique, values of one or more decision variables that optimizes the one or more key performance measures of the MCC process, to obtain optimized values of the one or more key performance measures, for each MCC configuration of the one or more MCC configurations, using the selected CC process model set, comprises:
   (a) generating initial values of the one or more decision variables, using the optimization technique;
   (b) obtaining sequence of chromatographic operations and a duration of each sequence of chromatographic operations at each stage of the MCC process, if the initial values of the one or more decision variables satisfies a feasibility criteria, wherein the feasibility criteria is associated with completion of regeneration protocol during a column switch and completion of predefined number of wash volumes;
   (c) calculating the one or more key performance measures of the MCC process by simulating the MCC process using the selected CC model set for the obtained sequence of chromatographic operations and the duration of the sequence of chromatographic operations, at each stage, until a cyclic steady state (CSS) of the MCC configuration is achieved, wherein in simulating the MCC process, inlet boundary condition for each of the column of the associated MCC configuration takes into account, the change in the operating conditions associated with each chromatographic operation and interconnected nature of column operations,
   wherein while simulating a wash operation and an elute operation, an inlet concentration $c_{in}$ is set equal to zero since monoclonal antibodies mAb is absent in the incoming buffer stream;
   wherein the one or more decision variables are associated with operating conditions to be maintained at each chromatographic operation of a set of chromatographic operations to be performed at each stage, and the one or more column characteristics of each column of one or more columns present in the MCC configuration;
   determine the optimum MCC configuration out of one or more MCC configurations, based on the associated optimized values of the one or more key performance measures of the MCC process, wherein the optimum MCC configuration is determined before a physical design of the MCC configuration significantly decreasing an amount of time, a material cost invested for designing the optimum MCC configuration,
   wherein the design of the MCC configuration meets purification targets and optimizing the one or more key performance measures; and
   display the optimal MCC configuration and along with the values of one or more decision variables associated with the optimized values of the one or more key performance measures through a display unit.

* * * * *